US008025053B1

(12) United States Patent
Prete et al.

(10) Patent No.: US 8,025,053 B1

(45) Date of Patent: Sep. 27, 2011

(54) PRESSURE REGULATOR ASSEMBLY

(75) Inventors: Christopher L. Prete, Cranberry Township, PA (US); John F. Rihn, Glenshaw, PA (US)

(73) Assignee: Mine Safety Appliances Company, Cranberry Township, PA (US)

( * ) Notice: Subject to any disclaimer, the term of this patent is extended or adjusted under 35 U.S.C. 154(b) by 290 days.

(21) Appl. No.: 10/606,456

(22) Filed: Jun. 26, 2003

(51) Int. Cl.

| | |
|---|---|
| ***A62B 7/04*** | (2006.01) |
| ***A62B 19/00*** | (2006.01) |
| ***A62B 9/02*** | (2006.01) |
| ***A62B 18/02*** | (2006.01) |
| ***A62B 7/10*** | (2006.01) |
| ***A62B 18/08*** | (2006.01) |
| ***A62B 18/10*** | (2006.01) |
| ***A61M 16/00*** | (2006.01) |

(52) U.S. Cl. ......... 128/204.26; 128/205.12; 128/205.24; 128/205.25; 128/205.27; 128/206.12; 128/206.17; 128/206.21; 128/206.28; 128/201.28; 128/202.29; 128/230.11; 128/201.25

(58) Field of Classification Search ............. 128/204.26, 128/205.12, 205.24, 205.25, 205.27, 206.12, 128/206.17, 206.21, 206.28, 201.28, 202.29, 128/203.11, 201.25

See application file for complete search history.

(56) References Cited

U.S. PATENT DOCUMENTS

| | | | | | |
|---|---|---|---|---|---|
| 3,935,861 | A | * | 2/1976 | Warncke | 128/204.26 |
| 3,969,174 | A | * | 7/1976 | Kelly et al. | 156/219 |
| 3,974,989 | A | * | 8/1976 | Goodfellow | 244/126 |
| 4,197,841 | A | * | 4/1980 | Brauer et al. | 128/202.13 |
| 4,211,822 | A | * | 7/1980 | Kurfman et al. | 428/412 |
| 4,253,455 | A | * | 3/1981 | Netteland | 128/204.26 |
| 4,276,877 | A | * | 7/1981 | Gdulla | 128/200.27 |
| 4,306,584 | A | * | 12/1981 | Schlobohm | 137/494 |
| 4,335,735 | A | * | 6/1982 | Cramer et al. | 137/81.1 |
| 4,345,592 | A | * | 8/1982 | Giorgini et al. | 128/204.26 |
| RE31,785 | E | * | 1/1985 | Netteland | 128/204.26 |

(Continued)

FOREIGN PATENT DOCUMENTS

EP 0 249 322 12/1987

OTHER PUBLICATIONS www.azom.com disclsoure regarding proeprties of PVF.*

(Continued)

*Primary Examiner* — Patricia Bianco

*Assistant Examiner* — Nihir Patel

(74) *Attorney, Agent, or Firm* — James G. Uber; Henry E. Bartony, Jr.

(57) ABSTRACT

A pressure demand regulator assembly for use with a breathing apparatus having a valve assembly that includes an inlet for connection to a source of breathing gas, an outlet for connection to a facepiece to provide breathing gas to the user and an actuator for controlling the flow of breathing gas between the inlet and the outlet in response to the user's respiration. The regulator assembly further includes a flexible elastomeric diaphragm in operative connection with the actuator. The diaphragm is exposed to ambient pressure on a first side thereof and exposed to a positive pressure within the facepiece on a second side thereof. The regulator assembly also includes an impermeable and flexible shield that seals the first side of the diaphragm from certain toxic substances in the ambient atmosphere while allowing the first side of the diaphragm to experience ambient pressure, such that the flexible shield moves along with the diaphragm during respiration without dampening the movement of the diaphragm during respiration of the user.

20 Claims, 4 Drawing Sheets

U.S. PATENT DOCUMENTS

| | | | | | |
|---|---|---|---|---|---|
| 4,594,285 | A | * | 6/1986 | Osawa et al. | 442/82 |
| 4,693,242 | A | * | 9/1987 | Biard | 128/204.26 |
| 4,765,980 | A | * | 8/1988 | DePrince et al. | 424/423 |
| 4,865,903 | A | * | 9/1989 | Adiletta | 428/215 |
| 4,898,582 | A | * | 2/1990 | Faste | 604/141 |
| 5,016,627 | A | | 5/1991 | Dahrendorf et al. | |
| 5,205,539 | A | * | 4/1993 | Schalk | 251/331 |
| 5,304,413 | A | * | 4/1994 | Bloom et al. | 428/215 |
| 5,318,018 | A | * | 6/1994 | Puma et al. | 128/202.11 |
| H1360 | H | * | 10/1994 | Grove et al. | 128/201.25 |
| 5,441,550 | A | * | 8/1995 | Hassenboehler et al. | 55/486 |
| 5,787,882 | A | * | 8/1998 | Hamilton | 128/204.26 |
| 5,811,359 | A | * | 9/1998 | Romanowski | 442/261 |
| 6,091,331 | A | * | 7/2000 | Toft et al. | 340/539.11 |
| 6,096,420 | A | * | 8/2000 | Wilhoit et al. | 428/343 |
| 6,394,091 | B1 | * | 5/2002 | Giorgini | 128/206.21 |
| 6,634,357 | B1 | * | 10/2003 | Hamilton | 128/205.24 |
| 6,892,725 | B2 | * | 5/2005 | Frund | 128/201.29 |
| 2003/0159692 | A1 | * | 8/2003 | Morgan et al. | 128/201.27 |
| 2004/0000311 | A1 | * | 1/2004 | Lowry | 128/204.26 |
| 2004/0149286 | A1 | * | 8/2004 | Haston | 128/204.26 |

OTHER PUBLICATIONS www.britannica.com disclosure regarding PVF.*

“Polyvinyl Fluoride.” Hawley’s Condensed Chemical Dictionary, 14th Edition. John Wiley & Sons, Inc.*

* cited by examiner

SECTION B-B

PRESSURE REGULATOR ASSEMBLY

BACKGROUND OF THE INVENTION

The present invention relates to a pressure regulator assembly and, especially, to a pressure regulator assembly for use with a breathing apparatus in an environment containing highly toxic substances.

A self contained breathing apparatus ("SCBA") is a device used to enable breathing in environments which are IDLH—immediately dangerous to life and health. For example, firefighters wear an SCBA when fighting a fire. The SCBA typically has a harness containing an air tank which is connected to a facepiece, all of which are worn or carried by the user. The tank typically contains air or gas under high pressure (2200 psi-4500 psi) and is connected to a first stage regulator which reduces the pressure to about 80 psi. The SCBA usually has a second stage regulator that has an inlet valve which controls the flow of air for breathing between the air tank and the facepiece. The valve controls the flow of air through the regulator in response to the respiration of the user. Such respiration-controlled regulator assemblies are disclosed, for example, in U.S. Pat. Nos. 4,821,767 and 5,016,627.

Typically, a diaphragm divides the regulator assembly into an inner chamber having a pressure corresponding to the pressure within facepiece of the SCBA and an outer chamber having a pressure corresponding to the surrounding environment, which is typically ambient pressure. The diaphragm is coupled to an actuating mechanism which opens and closes the inlet valve. The user's respiration creates a pressure differential between the inner and outer chambers of the regulator assembly which, in turn, causes displacement of the diaphragm thereby controlling (i.e., opening and closing) the inlet valve mechanism. As a result, such regulators are often called pressure demand regulators.

The facepiece of the SCBA is preferably maintained at a positive pressure as compared to the surrounding environmental pressure to prevent toxic gases and vapors in the environment from entering the facepiece. This positive pressure can, for example, be facilitated by biasing the diaphragm with a spring.

The positive pressure within the facepiece, however, may not be sufficient by itself to protect the user against unusually high concentrations of certain chemical and biological agents such as sarin ($C_4H_{10}FO_2P$, an extremely toxic chemical warfare agent that is a powerful cholinesterase inhibitor) or mustard agent ($C_4H_8Cl_2S$, an irritant vesicant oily liquid used especially as a chemical weapon). Although SCBAs are primarily constructed from thick-walled plastic, metal and rubber components, the diaphragm in the regulator assembly is often fabricated from an elastomeric material that is sufficiently porous and/or permeable to such highly toxic agents to allow dangerous levels thereof to enter the breathing system.

It is desirable, therefore, to develop a pressure regulator assembly suitable for use in environments including such highly toxic agents.

SUMMARY OF THE INVENTION

In one aspect, the present invention provides a regulator assembly for use with a facepiece of a breathing apparatus, comprising a valve assembly including an inlet for connection to a source of breathing gas, an outlet for connection to the facepiece to provide breathing gas to the facepiece and an actuator for controlling the flow of breathing gas between the inlet and the outlet. The regulator assembly further comprises a flexible elastomeric diaphragm in operative connection with the actuator. The diaphragm is exposed to ambient pressure on a first side thereof and exposed to a positive pressure within the facepiece on a second side thereof. The regulator assembly also comprises an impermeable and flexible shield that seals the first side of the diaphragm from certain toxic substances in the ambient atmosphere while allowing the first side of the diaphragm to experience ambient pressure, such that the flexible shield moves with the diaphragm during respiration. Preferably, the flexible shield does not significantly dampen the movement of the diaphragm during respiration so as to cause the regulator not to supply a sufficient air flow to maintain positive pressure in the facepiece. The flexible shield preferably has a thickness of less than 0.001 inches. The flexible shield can also be attached to a generally rigid base.

In one embodiment, the flexible shield is suitably impermeable such that in an atmosphere containing a concentration of distilled sulfur mustard agent vapor of 300 mg/m$^3$ for 30 minutes, the maximum peak excursion over six hours within the facepiece is no greater than 0.60 mg/m$^3$ nor is the maximum breakthrough integrated over the six hours greater than 6.0 mg-min/m$^3$ with the regulator delivering a measured air flow rate of 40 liters per minute. In another embodiment, the flexible shield is suitably impermeable such that in an atmosphere containing a concentration of liquid distilled sulfur mustard agent of 0.86 ml for six hours, the maximum peak excursion over six hours within the facepiece is no greater than 0.60 mg/m$^3$ nor is the maximum breakthrough integrated over the six hours greater than 6.0 mg-min/m$^3$ with the regulator delivering a measured air flow rate of 40 liters per minute. In still another embodiment, the flexible shield is suitably impermeable such that in an atmosphere containing a concentration of sarin vapor of 2,000 mg/m$^3$ for 30 minutes, the maximum peak excursion over six hours within the facepiece is no greater than 0.087 mg/m$^3$ nor is the maximum breakthrough integrated over the six hours greater than 2.1 mg-min/m$^3$ with the regulator delivering a measured air flow rate of 40 liters per minute. Preferably, the flexible shield is suitably impermeable to meet all of the above requirements. In one such embodiment, the flexible shield is formed from polyvinyl fluoride.

In another aspect, the present invention provides a shield assembly for sealing the diaphragm of a breathing apparatus regulator assembly from certain hazardous substances in the environment while allowing a first side of the diaphragm to experience environmental pressure, The shield assembly comprises a non-elastomeric, flexible, impermeable barrier film adjacent the first side of the diaphragm. The barrier film seals the diaphragm from the hazardous substances in the environment. Preferably, the barrier film does not significantly dampen the movement of the diaphragm during respiration so as to cause the regulator not to supply a sufficient air flow to maintain positive pressure in the facepiece. In one embodiment, the barrier film has a thickness of less than 0.001 inches. The barrier film can also be attached to a generally rigid base.

In one embodiment, the barrier film is suitably impermeable such that in an atmosphere containing a concentration of distilled sulfur mustard agent vapor of 300 mg/m$^3$ for 30 minutes, the maximum peak excursion over six hours within the facepiece is no greater than 0.60 mg/m$^3$ nor is the maximum breakthrough integrated over the six hours greater than 6.0 mg-min/m$^3$ with the regulator delivering a measured air flow rate of 40 liters per minute. In another embodiment, the barrier film is suitably impermeable such that in an atmosphere containing a concentration of liquid distilled sulfur mustard agent of 0.86 ml for six hours, the maximum peak excursion over six hours within the facepiece is no greater than 0.60 mg/m$^3$ nor is the maximum breakthrough integrated over the six hours greater than 6.0 mg-min/m$^3$ with the regulator delivering a measured air flow rate of 40 liters per minute. In still another embodiment, the barrier film is suitably impermeable such that in an atmosphere containing a concentration of sarin vapor of 2,000 mg/m$^3$ for 30 minutes, the maximum peak excursion over six hours within the facepiece is no greater than 0.087 mg/m$^3$ nor is the maximum breakthrough integrated over the six hours greater than 2.1 mg-min/m$^3$ with the regulator delivering a measured air flow rate of 40 liters per minute. Preferably, the barrier film is suitably impermeable to meet all of the above requirements. In one such embodiment, the barrier film is formed from polyvinyl fluoride.

In a further aspect, the present invention provides a method of sealing a diaphragm of a breathing apparatus regulator assembly from certain toxic or hazardous substances in the surrounding environment while allowing a first side of the diaphragm to experience environmental pressure. The method comprises the step of placing a non-elastomeric, flexible, impermeable barrier film adjacent the first side of the diaphragm, the barrier film sealing the diaphragm from certain toxic substances in the environment including chemical warfare agents such as sarin and mustard agent.

DETAILED DESCRIPTION OF THE INVENTION

Figure 1:
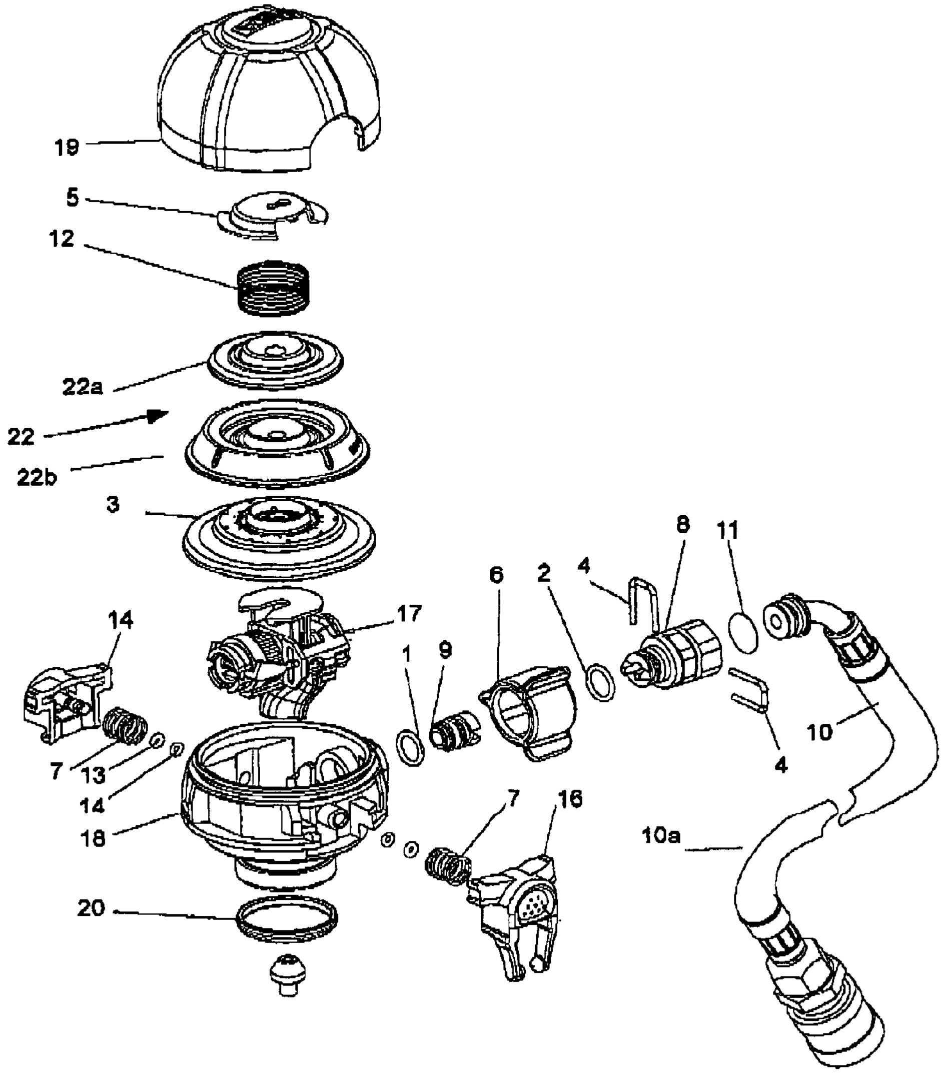
FIG. 1 illustrates an embodiment of a regulator assembly of the present invention in a disconnected or exploded state.
Figure 2:
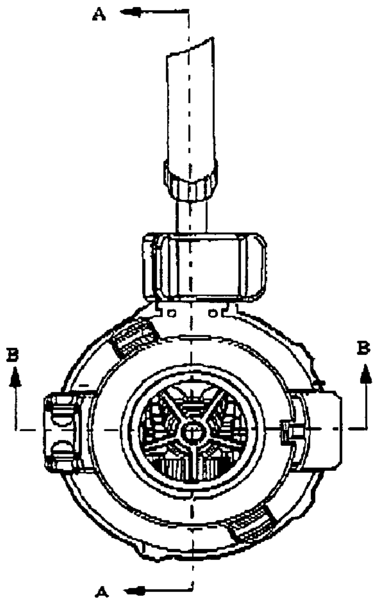
FIG. 2 illustrates a bottom view of the regulator assembly of FIG. 1.
Figure 3:
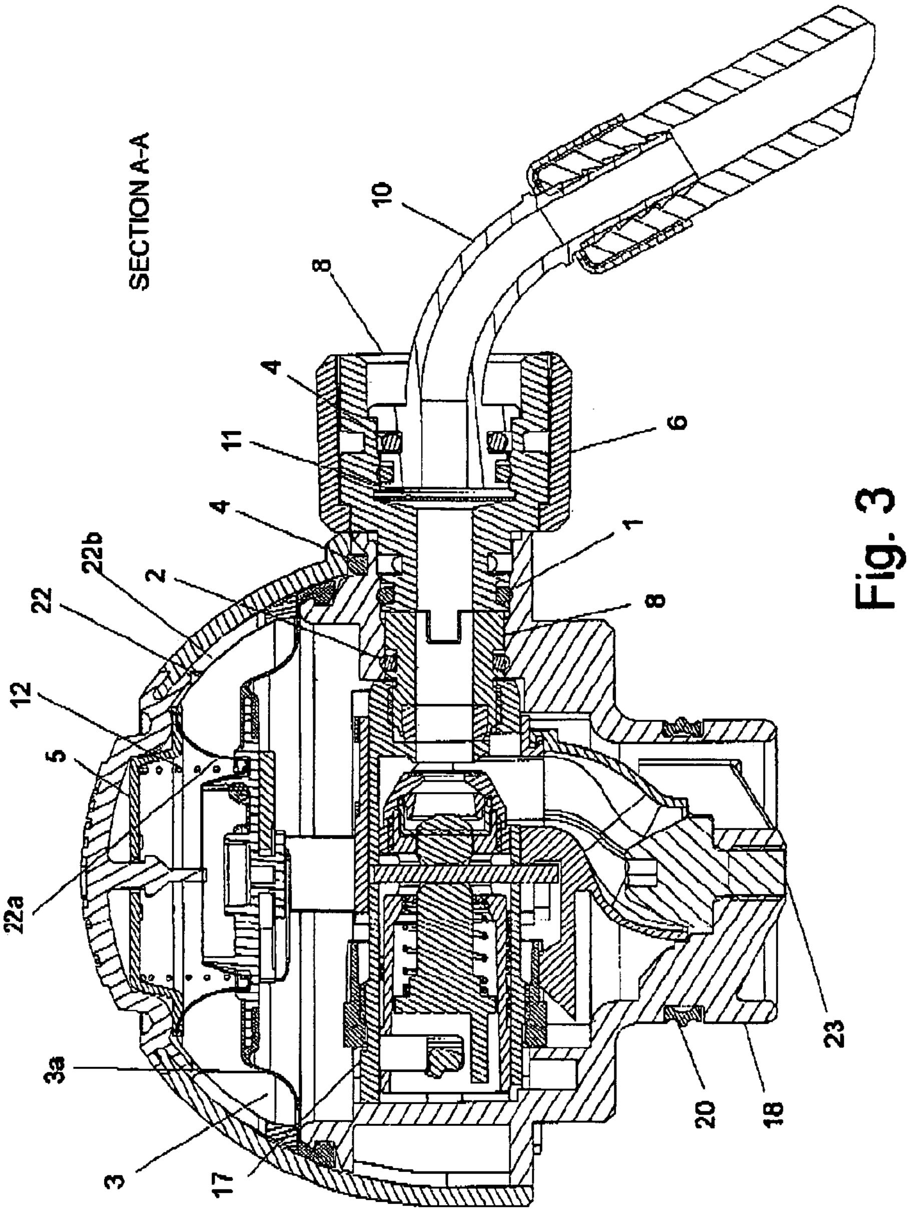
FIG. 3 illustrates a cross-sectional view of the regulator assembly of FIG. 1 through Section A-A as set forth in FIG. 2.
Figure 4:
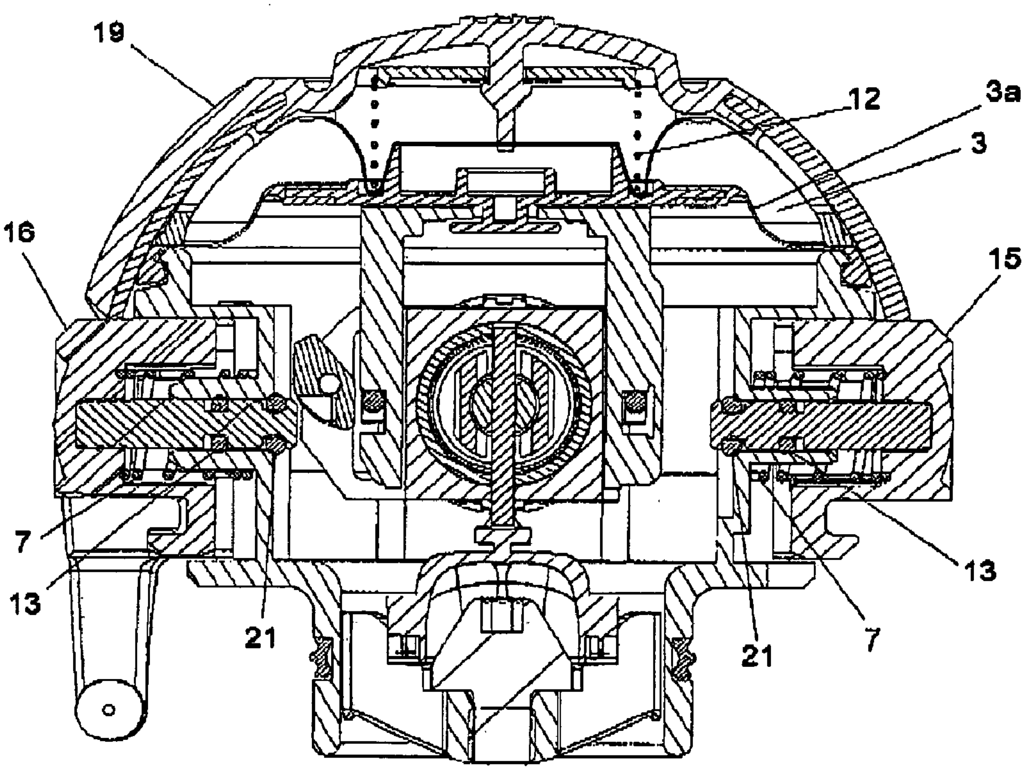
FIG. 4 illustrates a cross-sectional view of the regulator assembly of FIG. 1 through Section B-B as set forth in FIG. 2.

FIGS. 1 through 4 illustrate a preferred embodiment of a regulator assembly of the present invention similar in design and construction to the FIREHAWK™ mask mounted regulator currently available from Mine Safety Appliances Company of Pittsburgh, Pa. The list of parts shown therein is set forth in Table 1. The regulator assembly of the present invention, however, has been modified by adding shield assembly 22 to prevent certain chemical warfare agents and other toxic gases from permeating through the diaphragm of the regulator assembly and thus entering into the interior of the facepiece (not shown). The regulator assembly can, for example, be used with the ULTRA ELITE® facepiece available from Mine Safety Appliances Company.

TABLE 1

| Item | Description |
|---|---|
| 1 | O-Ring, Fluorsilicone |
| 2 | O-Ring, Silicone |
| 3 | Diaphragm Assembly |
| 4 | Uclip, (2 Req'd) |
| 5 | Retainer, Spring |
| 6 | Bypass, Knob |
| 7 | Spring, QC, (2 Req'd) |
| 8 | Body, Bypass |
| 9 | Bypass Insert Assembly |
| 10 | Hose Ass'y, 2nd Stg., Threaded |
| 11 | Hose Ass'y, 2nd Stg., Quick-Connect |
| 12 | Screen, Bypass |
| 13 | Spring, PD |
| 14 | O-Ring, Viton (2 Req'd) |
| 15 | O-Ring, Silicone (2 Req'd) |
| 16 | QC Button Assembly |
| 17 | Slidebutton Assembly |
| 18 | Valve Assembly w/Shutoff |
| 19 | Cover Assembly, Gray |
| 20 | O-Ring, Silicone |

Diaphragm assembly 3 of the regulator assembly includes a flexible, elastomeric diaphragm 3*a* as known in the art. Elastomeric diaphragm 3*a*, on the upper side thereof (in the orientation of FIGS. 1, 3 and 4) is exposed to ambient pressure via openings in regulator cover assembly 19. On its lower side, elastomeric diaphragm 3*a* is exposed to the positive pressure of the facepiece (that is, a pressure higher than ambient pressure). Elastomeric diaphragm 3*a* is biased in connection with an actuator of valve assembly 17 via a spring 12, which also biases valve assembly 17 to assist in ensuring that a positive pressure is maintained within the facepiece. Upon inhalation by the user, elastomeric diaphragm 3*a* is drawn downward from the generally relaxed state illustrated in FIGS. 3 and 4 and thereby opens valve assembly 17, which is connected to a supply of breathing air or gas (via, for example, a connective hose assembly 10), to allow pressurized air or gas to enter the facepiece. Upon exhalation, elastomeric diaphragm 3*a* returns to the position illustrated in FIGS. 3 and 4 and the valve assembly 17 is closed.

Elastomeric materials such as the material used for elastomeric diaphragm 3*a* are sufficiently permeable to certain highly toxic and hazardous substances (for example, sarin or mustard agent) to allow unsafe concentrations of such substances to build up within the facepiece in environments containing high concentrations of such substances. Unlike currently available regulator assemblies, flexible, elastomeric diaphragm 3*a* of the present invention, is separated from such substances in the ambient environment by a nonporous, impermeable cover, shield, or barrier assembly 22 positioned between spring 12 and diaphragm assembly 3. Shield assembly 22 prevents toxic and other hazardous substances from coming into contact with elastomeric diaphragm 3*a*. Shield assembly 22 comprises a generally flexible or flexing portion 22*a* which transmits ambient pressure to elastomeric diaphragm 3*a* and moves with the respiration-driven movement of elastomeric diaphragm 3*a*. Preferably, flexing portion 22*a* requires little force exerted upon it to move along with elastomeric diaphragm 3*a*. In that regard, flexing portion 22*a* should not dampen the motion of elastomeric diaphragm 3*a* to a degree such that positive pressure cannot be maintained on the facepiece side of elastomeric diaphragm 3*a*.

As elastomeric materials are generally unsuitable to act as a barrier to high concentrations of certain toxic substances such as chemical warfare agents, shield assembly 22 of the present invention was fabricated from a very thin layer of a non-elastomeric, nonporous, impermeable material. In one embodiment, a polyvinyl fluoride (TEDLAR®, available from Dupont) film having a thickness of approximately 0.5 mil (0.0005 inches) was used for flexing portion 22*a*. It was discovered that polyvinyl fluoride at this thickness moved readily with elastomeric diaphragm 3*a* without significantly damping the motion thereof. Moreover, polyvinyl fluoride of that thickness also provided a suitable barrier to toxic substances such as sarin and mustard gas as determined under standards which have been established for chemical agent permeation and penetration resistance against sarin (GB) and mustard agent (HD) under NIOSH. 42 CFR 84.63(c). A Statement of Standard for the testing protocol is attached hereto as Attachment A and is incorporated herein by reference. The test requirements are summarized in Tables 2 and 3 below.

TABLE 2

Simultaneous Liquid and Vapor Challenge of SCBA with Distilled Sulfur Mustard

| Challenge Agent | Challenge Concentration | Duration of Challenge (min) | Breathing Machine Airflow Range (L/min) | Maximum Peak Excursion ($mg/m^3$) | Maximum Breakthrough (concentration integrated over Minimum Service Life) ($mg\text{-}min/M^3$) | Number of Systems Tested | Minimum Service Life (hours) |
|---|---|---|---|---|---|---|---|
| HD-Vapor | 300 $mg/m^3$ | 30 | 40 | 0.60 | 6.0 | 3 | 6 |
| HD-Liquid | 0.86 ml | 360 | | | | | |

TABLE 3

Vapor Challenge of SCBA with Sarin (GB)

| Challenge Agent | Challenge Concentration | Duration of Challenge (min) | Breathing Machine Airflow Range (L/min) | Maximum Peak Excursion ($mg/m^3$) | Maximum Breakthrough (concentration integrated over Minimum Service Life) ($mg\text{-}min/M^3$) | Number of Systems Tested | Minimum Service Life (hours) |
|---|---|---|---|---|---|---|---|
| GB-Vapor | 2,000 $mg/m^3$ | 30 | 40 | 0.087 | 2.1 | 3 | 6 |

In the above tests, an SCBA having a regulator assembly of the present invention was exposed to the challenge concentration for 30 minutes after which the flow of a vapor challenge agent into the test chamber was stopped. The SCBA remained in the test chamber for a total of 6 hours under a continually decreasing challenge concentration. A liquid HD challenge agent remained on the SCBA for the full 6 hours.

In addition to the chemical agents described above and other chemical agents, shield assembly 22 can also provide a barrier to certain biological, radiological and nuclear agents.

The regulator assembly of the present invention, including shield assembly 22 often will be used in harsh environments over a wide range of ambient conditions. If used in firefighting applications, the regulator assembly of the present invention must comply with the National Fire Protection Association (NFPA) standards. See NFPA Standards for Open-Circuit Self-Contained Breathing Apparatus For Fire and Emergency Services 1981 (2002 Version), the disclosure of which is incorporated herein by reference. Particularly relevant among those standards for the purpose of determining suitable materials for shield assembly 22 are the temperature related tests. See, for example, Section 7.2 Environmental Temperature Performance and sections of Chapter 8 referenced therein. During such testing, the regulator assembly and shield assembly 22 can experience temperatures varying from −70° F. to over 1000° F. for certain periods of time, which are designed to simulate the extreme conditions experienced during actual use in firefighting and emergency situations. The shield assembly 22 does not dampen the diaphragm assembly 3 significantly enough to cause the regulator assembly not to supply sufficient air flow to maintain a positive pressure in the facepiece for the durations and breathing rates specified by NFPA 1981 at temperature extremes ranging from −70° F. to 1000° F.

In view of this, the materials chosen for shield assembly 22 should preferably operate over a wide range of temperatures. For example, flexible portion 22*a*, should maintain its flexibility even at low temperatures as described above without becoming brittle in a manner that could damage flexible portion 22*a* and cause it to become permeable. Likewise, the permeability of polymers often increase substantially above the polymers' glass transition temperature ($T_g$). The material for flexible portion 22*a* thus preferably has a $T_g$ above 200° F. More preferably, the material for flexible portion 22*a* has a $T_g$ above 300° F.

In the embodiment of FIGS. 1 through 4, shield assembly 22 further includes a generally rigid, outer ring or base portion 22*b* which forms a seal with flexible portion 22*a* and with diaphragm assembly 3. In one embodiment, base portion 22*b* was fabricated from glass-filled nylon. Flexible portion 22*a* can, for example, be adhered directly to base portion 22*b* or can be adhered thereto via an intermediate, double-sided adhesive film. Flexible portion 22*a* can also be molded directly into ring or base portion 22*b* or have a snap fit assembly securing it to base portion 22*b*.

In one embodiment, outer ring or base portion 22*b* was injection molded in a split cone shape. In forming flexible portion 22*a*, a thin, flat, chemical barrier film such as polyvinyl fluoride was attached to the wider bottom of base portion 22*b* by affixing a double-sided adhesive film between the barrier film base portion 22*b*. The base portion/film assembly was then placed in a vacuum-forming fixture and heated to a temperature above the softening point of the barrier film. Upon heating, the barrier film was simultaneously drawn into a cavity using a vacuum molding technique. The barrier film retained the shape of the cavity upon removal from the fixture.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A regulator assembly for use in a breathing apparatus, comprising:

a valve assembly including an inlet for connection to a source of breathing gas, an outlet for connection to a facepiece to provide breathing gas to a user and an actuator for controlling flow of breathing gas between the inlet and the outlet;

a flexible elastomeric diaphragm in operative connection with the actuator, the diaphragm being exposed to force from ambient pressure on a first side thereof and being exposed to a positive pressure within the facepiece on a second side thereof, and a flexible shield that is non-elastomeric and impermeable and that is formed separate from and positioned adjacent to the diaphragm, the flexible shield being movable with the diaphragm during respiration of the user, the flexible shield being in fluid connection with the ambient atmosphere on a first side of the flexible shield and in operative connection with the first side of the diaphragm on a second side of the flexible shield which is opposite the first side of the flexible shield, the flexible shield sealing the first side of the diaphragm from fluid contact with the ambient atmosphere and thereby from toxic substances in the ambient atmosphere while transmitting force from ambient pressure to the first side of the diaphragm, the diaphragm being more porous or more permeable to toxic substances than the flexible shield.

2. The regulator assembly of claim 1 wherein the flexible shield does not significantly dampen the movement of the diaphragm.

3. The regulator assembly of claim 1 wherein the flexible shield has a thickness of less than 0.001 inches.

4. The regulator assembly of claim 3 wherein the flexible shield is formed from polyvinyl fluoride.

5. The regulator assembly of claim 1 wherein the flexible shield is formed from polyvinyl fluoride.

6. The regulator assembly of claim 1 wherein the flexible shield is suitably impermeable such that in an atmosphere containing a concentration of distilled sulfur mustard agent vapor of 300 $mg/m^3$ for 30 minutes, the maximum peak excursion over six hours within the facepiece is no greater than 0.60 $mg/m^3$ with the regulator delivering a measured air flow rate of 40 liters per minute.

7. The regulator assembly of claim 1 wherein the flexible shield is suitably impermeable such that in an atmosphere containing a concentration of liquid distilled sulfur mustard agent of 0.86 ml for six hours, the maximum peak excursion over six hours within the facepiece is no greater than 0.60 $mg/m^3$ with the regulator delivering a measured air flow rate of 40 liters per minute.

8. The regulator assembly of claim 1 wherein the flexible shield is suitably impermeable such that in an atmosphere containing a concentration of sarin vapor of 2,000 $mg/m^3$ for 30 minutes, the maximum peak excursion over six hours within the facepiece is no greater than 0.087 $mg/m^3$ with the regulator delivering a measured air flow rate of 40 liters per minute.

9. The regulator assembly of claim 1 wherein the flexible shield is attached to a generally rigid base.

10. An assembly for a breathing apparatus regulator assembly, comprising: a diaphragm and a flexible barrier film that is both non-elastomeric and impermeable, the barrier film being formed separate from and positioned adjacent to a first side of a diaphragm, the barrier film being movable with the diaphragm during respiration, the barrier film positioned to be in fluid connection with the ambient atmosphere on a first side of the barrier film and in operative connection with the first side of the diaphragm on a second side of the barrier film which is opposite the first side of the barrier film, the barrier film sealing the diaphragm from fluid contact with the ambient atmosphere and thereby from hazardous substances in the environment while transmitting force resulting from environmental pressure to first side of the diaphragm, the diaphragm being more porous or more permeable to hazardous substances than the barrier film.

11. The assembly of claim 10 wherein the barrier film does not significantly dampen the movement of the diaphragm.

12. The assembly of claim 11 wherein the barrier film has a thickness of less than 0.001 inches.

13. The assembly of claim 12 wherein the barrier film is formed from polyvinyl fluoride.

14. The assembly of claim 13 wherein the barrier film is suitably impermeable such that in an atmosphere containing a concentration of liquid distilled sulfur mustard agent of 0.86 ml for 30 minutes, the maximum peak excursion over six hours within a facepiece in operative connection with the assembly is no greater than 0.60 $mg/m^3$ with the regulator delivering a measured air flow rate of 40 liters per minute.

15. The assembly of claim 13 wherein the barrier film is suitably impermeable such that in an atmosphere containing a concentration of sarin vapor of 2,000 $mg/m^3$ for 30 minutes, the maximum peak excursion over six hours within the breathing apparatus is no greater than 0.087 $mg/m^3$ with the regulator delivering a measured air flow rate of 40 liters per minute.

16. The assembly of claim 13 wherein the barrier film is attached to a generally rigid base.

17. The assembly of claim 10 wherein the barrier film has a thickness of less than 0.001 inches.

18. The assembly of claim 17 wherein the barrier film is suitably impermeable such that in an atmosphere containing a concentration of distilled sulfur mustard agent vapor of 300 $mg/m^3$ for 30 minutes, the maximum peak excursion over six hours within a facepiece in operative connection with the assembly is no greater than 0.60 $mg/m^3$ with the regulator delivering a measured air flow rate of 40 liters per minute.

19. The assembly of claim 10 wherein the barrier film is formed from polyvinyl fluoride.

20. A method of sealing a diaphragm of a breathing apparatus regulator assembly from toxic substances in the environment while allowing a first side of the diaphragm to experience force from environmental pressure, comprising: placing a flexible barrier film that is both non-elastomeric and impermeable and is formed separate from the diaphragm adjacent to the first side of the diaphragm, the barrier film being movable with the diaphragm during respiration, the barrier film positioned to be in fluid connection with the ambient atmosphere on a first side of the barrier film and in operative connection with the first side of the diaphragm on a second side of the barrier film which is opposite the first side of the barrier film, the barrier film transmitting force from ambient pressure to the first side of the diaphragm and sealing the diaphragm from fluid contact with the environment and thereby from the toxic substances in the environment without significantly dampening the movement of the diaphragm, the diaphragm being more porous or more permeable to toxic substances than the barrier film.

* * * * *